(12) United States Patent
Shimada et al.

(10) Patent No.: US 7,100,425 B2
(45) Date of Patent: Sep. 5, 2006

(54) HYDROGEN SENSOR

(75) Inventors: Toshiaki Shimada, Wako (JP); Yoshio Nuiya, Wako (JP)

(73) Assignee: Honda Motor Co., Ltd., Tokyo (JP)

( * ) Notice: Subject to any disclaimer, the term of this patent is extended or adjusted under 35 U.S.C. 154(b) by 7 days.

(21) Appl. No.: 10/942,707

(22) Filed: Sep. 15, 2004

(65) Prior Publication Data
US 2005/0067281 A1    Mar. 31, 2005

(30) Foreign Application Priority Data
Sep. 30, 2003   (JP)   ............... 2003-340169

(51) Int. Cl.
*G01N 7/00*  (2006.01)
(52) U.S. Cl. .................................... 73/31.06
(58) Field of Classification Search ............... 73/31.06, 73/23.2; 422/88, 98; 338/34
See application file for complete search history.

(56) References Cited

U.S. PATENT DOCUMENTS 5,279,795 A * 1/1994 Hughes et al. ............. 422/98
6,155,099 A * 12/2000 Kobayashi et al. ........ 73/31.05
6,596,236 B1 * 7/2003 DiMeo et al. ............... 422/88
6,705,152 B1 * 3/2004 Routkevitch et al. ...... 73/31.05
6,849,911 B1 * 2/2005 Monty et al. ............... 257/414
2005/0028580 A1 * 2/2005 Bauer et al. ............... 73/25.03

FOREIGN PATENT DOCUMENTS

JP          10-73530         3/1998

\* cited by examiner

*Primary Examiner*—Hezron Williams
*Assistant Examiner*—Ryan Christensen
(74) *Attorney, Agent, or Firm*—Hamre, Schumann, Mueller & Larson, P.C.

(57) ABSTRACT

A hydrogen sensor 1 includes detection elements 4A, 4B, 4C formed from hydrogen-absorbing alloys which exhibit different hydrogen-absorbing pressures at a given temperature; a strain gauge 6 which detects changes in volume upon absorbing of hydrogen by the detection elements 4A, 4B, 4C; a micro-heater 2 which controls the temperatures of all the detection elements 4A, 4B, 4C to approximate equal values; and a substrate 3.

6 Claims, 2 Drawing Sheets

H < 0.5

0.5% ≤ H < 1.0%

1.0% ≤ H < 2.0%

H ≥ 2.0%

HYDROGEN SENSOR

This application claims foreign priority based on Japanese Patent application No. 2003-340169, filed Sep. 30, 2003, the contents of which is incorporated herein by reference in its entirety.

BACKGROUND OF THE INVENTION

1. Field of the Invention

The present invention relates to a hydrogen sensor for detecting hydrogen concentration in a gas.

2. Description of the Related Art

As a related art, a hydrogen sensor utilizing a hydrogen-absorbing alloy is disclosed in JP-A-10-73530. The hydrogen sensor has a hydrogen-absorbing alloy bonded on one surface of its substrate and has a strain gauge attached on the other surface thereof. In this arrangement, the distortion is produced in the substrate under a circumstance of volume expansion caused in the course of absorbing hydrogen by the hydrogen alloy. The hydrogen sensor detects the amount of said absorbed hydrogen by the strain gauge on the basis of a magnitude of distortion of a substrate. The hydrogen sensor utilizing such a hydrogen-absorbing alloy shows fairly high selectivity of hydrogen, whereby the hydrogen sensor has an advantage of high detection accuracy.

The hydrogen sensor as disclosed in JP-A-10-73530 is suitable for detecting an amount of hydrogen, for instance, in such a way of being incorporated in equipment utilizing a hydrogen-absorbing alloy (e.g., hydrogen-absorbing alloy tank); however, the sensor is incapable of detecting a hydrogen concentration in a gas.

SUMMARY OF THE INVENTION

The present invention provides a hydrogen sensor which enables detection of a concentration of a hydrogen gas contained in the atmosphere by utilizing a hydrogen-absorbing alloy having high selectivity for hydrogen.

To solve the above problem, the invention as set forth in the first aspect provides a hydrogen sensor (e.g., a hydrogen sensor 1 in an embodiment to be described later) includes a plurality of detection elements 4A, 4B, and 4C (e.g., hydrogen-absorbing alloys MH-1, MH-2, MH-3 in an embodiment which will be described later); detection means (e.g., a strain gauge 6 in the embodiment which will be described later) for detecting changes in a property upon absorbing of hydrogen by the respective detection elements; and temperature control means (e.g., a micro-heater 2 and substrate 3 in the embodiment which will be described later).

A hydrogen-absorbing alloy forming the detection element does not absorb hydrogen when the hydrogen partial pressure of the atmosphere surrounding the hydrogen sensor is lower than a hydrogen-absorbing pressure corresponding to a temperature; however, the hydrogen-absorbing alloy starts absorbing of hydrogen when the hydrogen partial pressure reaches the hydrogen-absorbing pressure corresponding to the temperature. When hydrogen is absorbed in the hydrogen-absorbing alloy, properties of the hydrogen-absorbing alloy, such as volume, temperature, and weight might be changed. Hence the hydrogen sensor can determine that the detection element absorbed hydrogen.

Meanwhile, the hydrogen-absorbing alloys forming the respective detection elements differ from each other in terms of pressure-temperature (P-T) characteristics. Accordingly, when temperatures of a plurality of detection elements are controlled to approximate identical values, a concentration range of hydrogen of an atmosphere surrounding the hydrogen detector can be detected on the basis of which detection element absorbs hydrogen.

Furthermore, since the hydrogen-absorbing alloy forming the detection element has fairly high selectivity for hydrogen, accuracy in concentration detection is increased.

An invention as the second aspect based on the first aspect is characterized in that thermal insulation means (e.g., a heat insulation layer 5 in the embodiment which will be described later) is interposed between adjacent detection elements.

By virtue of the above configuration, thermal interference between adjacent detection elements can be prevented.

An invention as the third aspect based on the invention of the first or second aspects is characterized in that the property is volume, electrical resistance, or weight.

The above configuration enables easy detection of changes in the property upon absorbing of hydrogen by the hydrogen-absorbing alloy forming the detection element.

According to the invention set forth in the first aspect, the hydrogen sensor includes a plurality of detection elements formed from hydrogen-absorbing alloys which differ in terms of hydrogen-absorbing pressure at a given temperature. Therefore, a hydrogen concentration range of the atmosphere surrounding the hydrogen sensor can be detected on the basis of which detection element absorbs hydrogen. Furthermore, since the hydrogen-absorbing alloy forming the detection element has fairly high selectivity for hydrogen, accuracy in concentration detection is high.

According to the invention set forth in the second aspect, thermal interference between adjacent detection elements can be prevented. Accordingly, even when the hydrogen-absorbing alloy of either one of the detection elements produces heat upon absorbing of hydrogen, the adjacent detection element can be protected from thermally influence. That is, temperature control of the adjacent detection element can be protected from adverse effects.

According to the invention set forth in the third aspect, changes in the property upon absorbing of hydrogen by the hydrogen-absorbing alloy forming the detection element can be easily detected.

DESCRIPTION OF THE PREFERRED EMBODIMENTS

Embodiments of a hydrogen sensor according to the invention will be described with reference to FIGS. 1 to 4.

Figure 1:
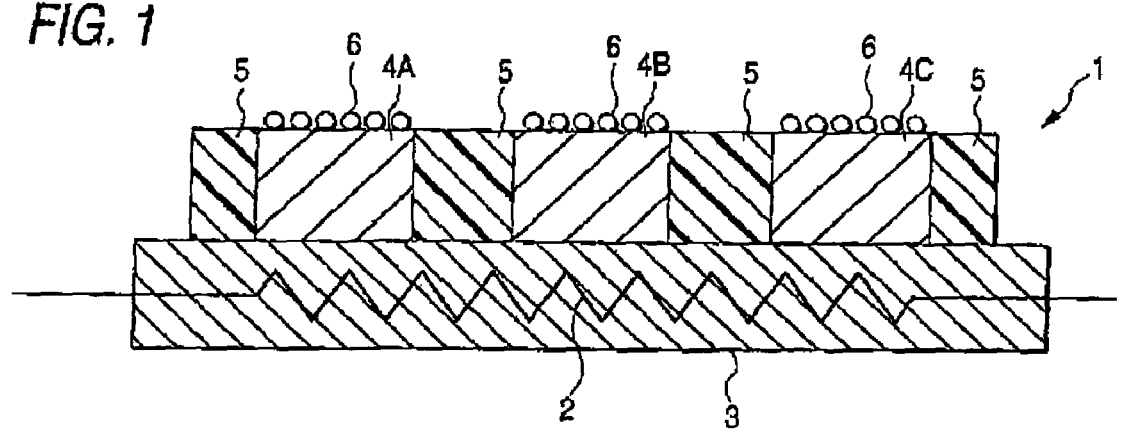
FIG. 1 is across-sectional view of a hydrogen sensor according to the present invention.

As shown in FIG. 1, the hydrogen sensor 1 comprises a substrate 3 in which a micro-heater is buried; a plurality of (in the embodiment, three) detection elements 4A, 4B, 4C (denoted as "detection elements 4" when particular identification thereof is not required) disposed on the upper surface of the substrate 3; heat insulation layers 5 (thermal insulating means) which are disposed around the respective detection elements so as to separate the adjacent detection elements 4, 4; and a strain gauge (detection means) 6 attached on the upper surface of each of the detection elements 4.

The substrate 3 serves as a support for integrally supporting the three detection elements 4A, 4B, 4C, and also serves as a temperature-maintaining device for holding the temperatures of the detection elements 4A, 4B, 4C at approximate equal values. A micro-heater 2 of the detection element is disposed so that it can regulate the entire substrate 3 at an approximately uniform temperature, and can control the temperature of the substrate 3 at a predetermined target value by means of current control by an controller that is not illustrated. In the embodiment, the substrate 3 and the micro-heater 2 constitute the temperature control means.

The detection elements 4 are bonded firmly on the substrate 3 by appropriate means having superior heat resistance, such as sintering, crimping, thermal spraying, or adhesion, so as to prevent occurrence of clearance between adjacent detection elements 4. For instance, the detection elements 4 are bonded by means of coating the substrate 3 with a hydrogen-absorbing alloy assuming the form of slurry.

Figure 4:
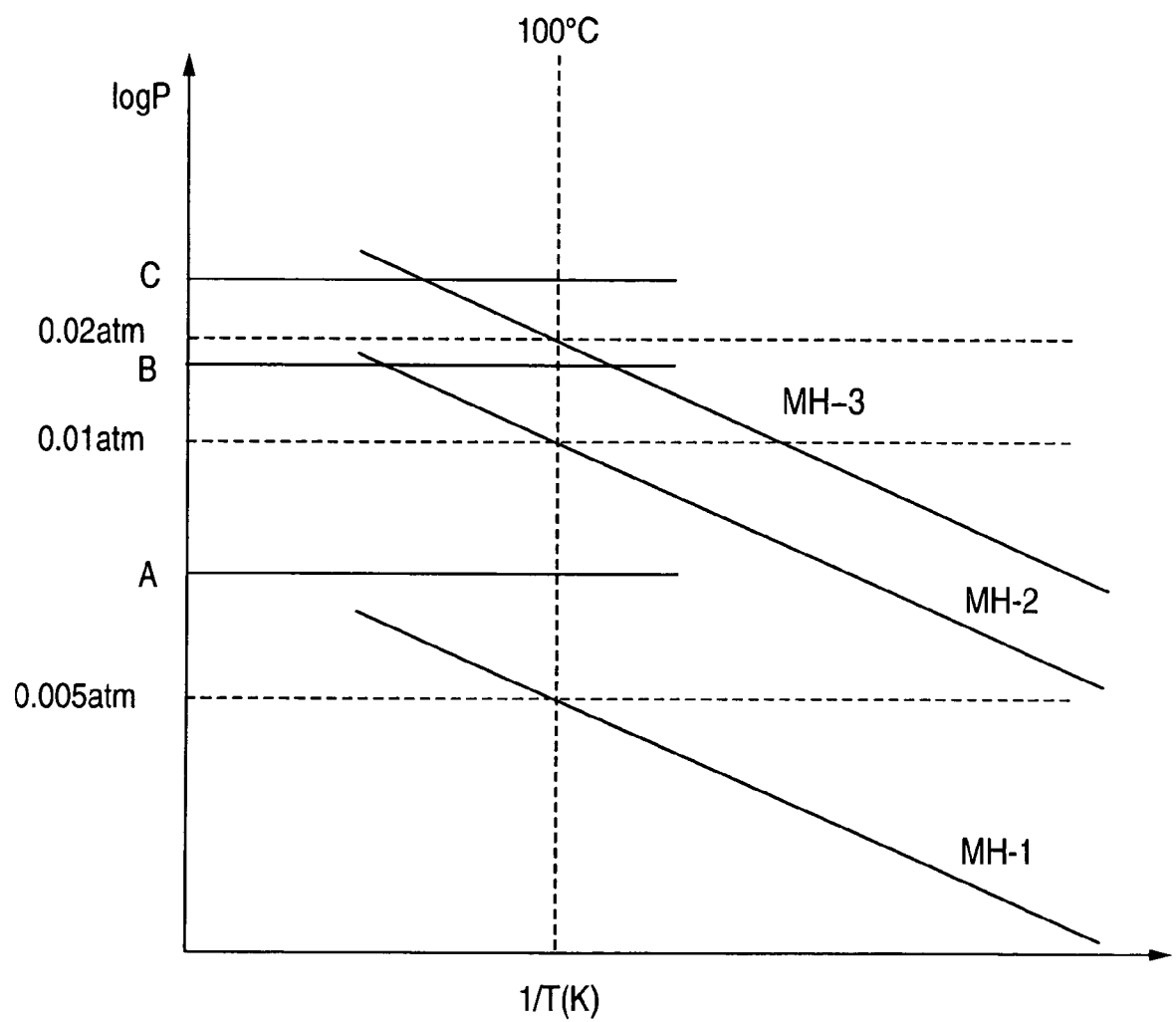
FIG. 4 is a diagram showing P-T characteristics of hydrogen-absorbing alloys used in the hydrogen sensor.

The detection elements 4A, 4B, 4C are formed from hydrogen-absorbing alloys MH-1, MH-2, MH-3 whose P-T characteristics differ from each other. FIG. 4 shows P-T characteristics of the hydrogen-absorbing alloys MH-1, MH-2, MH-3 used in the detection elements 4A, 4B, 4C of the embodiment. The vertical axis represents logarithm of hydrogen-absorbing pressure (log P), and the horizontal axis represents the inverse of absolute temperature (1/T) of each of the hydrogen-absorbing alloys. For all the hydrogen-absorbing alloys MH-1, MH-2, MH-3, hydrogen-absorbing pressure increases with temperature of the hydrogen-absorbing alloy, and the respective hydrogen-absorbing alloys exhibit substantially identical rates of change in hydrogen-absorbing pressure with respect to temperature. For a given temperature, the hydrogen-absorbing alloys are in the following order in terms of increasing hydrogen-absorbing pressure: the hydrogen-absorbing alloy MH-1 of the detection element 4A, the hydrogen-absorbing alloy MH-2 of the detection element 4B, and the hydrogen-absorbing alloy MH-3 of the detection element 4C.

The operation temperature of the hydrogen sensor 1 is set at 100° C. in the embodiment. At the operation temperature 100° C., the respective hydrogen-absorbing pressures are as follows: that of the hydrogen-absorbing alloy MH-1 is 0.005 atmosphere; that of the hydrogen-absorbing alloy MH-2 is 0.01 at; and that of the hydrogen-absorbing alloy MH-3 is 0.02 atmosphere.

From a relation between hydrogen partial pressure and hydrogen concentration in the atmosphere, hydrogen partial pressures of 0.005 atmosphere, 0.01 atmosphere, and 0.02 atmosphere correspond to hydrogen concentrations of 0.5%, 1.0%, and 2.0%, respectively.

Furthermore, the hydrogen-absorbing alloy has characteristics that, upon absorbing of hydrogen, volume increases, heat is produced, and weight increases.

The heat insulation layer 5 prevents thermal interference between the adjacent detection elements 4, 4. Therefore, even when the hydrogen-absorbing alloy of either one of the detection elements 4, 4 produces heat upon absorbing of hydrogen, the heat insulation layer 5 can prevent the adjacent detection element 4 from being affected by the heat, thereby allowing the temperature of the adjacent detection element 4 to be controlled to a target value.

Figure 2:
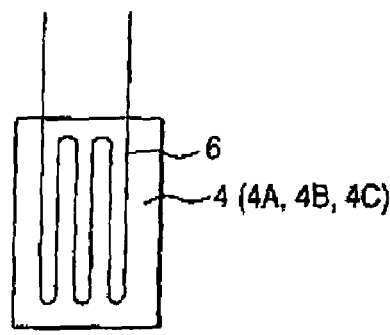
FIG. 2 is a plain view of a detection element of the hydrogen sensor.

As shown in FIGS. 1 and 2, the strain gauge 6 is integrally bonded on the upper surface of the respective detection elements 4 by means of heat-resistant adhesive, or the like, and the strain gauge 6 per se is also heat-resistant. The strain gauge 6 detects distortion as a change in electrical resistance appearing when the hydrogen-absorbing alloy forming the detection elements 4 is expanded in volume upon absorbing of hydrogen. The respective gauges 6 are connected to a detection circuit not shown. Furthermore, the detection circuit is configured so as to illuminate corresponding concentration lamps L1 to L3 of a display device shown in FIGS. 3(*a*) to 3(*d*) when the detection circuit detects distortion. Note that the concentration lamps L1 to L3 correspond to the detection elements 4A to 4C respectively, and solid circles in FIGS. 3(*a*) to 3(*d*) indicate that the respective lamps are illuminating.

Next, operations of the hydrogen detector 1 will be described.

A hydrogen-absorbing alloy forming the detection element 4 does not absorb hydrogen when a hydrogen partial pressure of the atmosphere surrounding the hydrogen sensor 1 is lower than a hydrogen-absorbing pressure corresponding to the temperature; however, the hydrogen-absorbing alloy starts absorbing of hydrogen when the hydrogen partial pressure reaches the hydrogen-absorbing pressure corresponding to the temperature. The hydrogen-absorbing alloy expands in volume upon absorbing of hydrogen, whereby the detection circuit detects changes in electrical resistance in the strain gauge 6 attached to the detection element 4. In other words, the detection element 4, whose distortion is detected by the strain gauge 6, is assumed to absorb hydrogen.

Meanwhile, the hydrogen-absorbing alloys MH-1, MH-2, MH-3 respectively forming the three detection elements of 4A, 4B, 4C differ in terms of P-T characteristics. Accordingly, when temperatures of the three detection elements 4 are controlled to substantially equal values, a concentration range of hydrogen of the atmosphere surrounding the hydrogen sensor 1 can be detected on the basis of which detection element(s) 4 absorbs hydrogen.

A specific method for detecting hydrogen concentration will now be described. As described above, the operation temperature of the hydrogen detector 1 is set at 100° C. in the embodiment. Accordingly, the temperatures of the detection elements 4A, 4B, 4C are controlled at 100° C. by way of the substrate 3, by means of controlling the micro-heater 2.

When the temperatures of the hydrogen-absorbing alloys 4A, 4B, 4C are maintained at 100° C., a hydrogen-absorbing pressure of the hydrogen-absorbing alloy MH-1 of the detection element 4A is 0.005 atmosphere, a hydrogen-absorbing pressure of the hydrogen-absorbing alloy MH-2 of the detection element 4B is 0.01 atmosphere, and a hydrogen-absorbing pressure of the hydrogen-absorbing alloy MH-3 of the detection element 4C is 0.02 atmosphere.

Figure 3A:
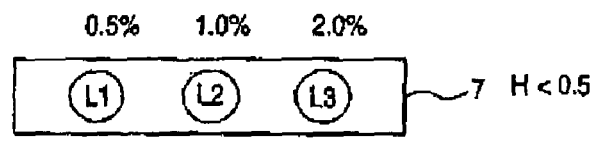
FIGS. 3(a) to 3(d) are display examples for hydrogen concentration on a display device of the hydrogen sensor.

Therefore, when a hydrogen partial pressure of the atmosphere surrounding the hydrogen sensor 1 is lower than 0.005 atmosphere, the hydrogen partial pressure is lower than any of the hydrogen-absorbing pressures of the hydrogen-absorbing alloys MH-1, MH-2, MH-3. Therefore, the hydrogen-absorbing alloys MH-1, MH-2, and MH-3 do not absorb hydrogen, and the respective strain gauges of the detection elements 4A, 4B, 4C do not detect distortion. Consequently, as shown in FIG. 3A, none of the concentration lamps L1 to L3 of the display device 7 is illuminated. In this case, a hydrogen concentration of the atmosphere is lower than 0.5%.

Figure 3B:
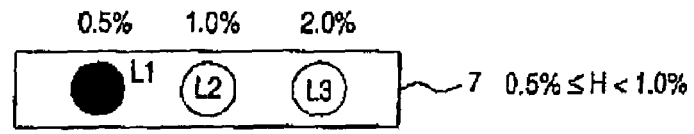

When the hydrogen partial pressure of the atmosphere is at least 0.005 atmosphere and lower than 0.01 atmosphere (A in FIG. 4), the hydrogen partial pressure is higher than or equal to the hydrogen-absorbing pressure of the hydrogen-absorbing alloy MH-1. Accordingly, the hydrogen-absorbing alloy MH-1 absorbs hydrogen and expands in volume; and the strain gauge 6 of the detection element 4A detects distortion. However, the hydrogen partial pressure is lower than the hydrogen-absorbing pressures of the hydrogen-absorbing alloys MH-2, MH-3. Accordingly, the hydrogen-absorbing alloys MH-2 and MH-3 do not absorb hydrogen, and none of the strain gauges 6 of the detection elements 4B, 4C detects distortion. Consequently, as shown in FIG. 3B, only the concentration lamp L1 of the display device 7 illuminates, and the concentration lamps L2, L3 do not illuminate. In this case, a hydrogen concentration of the atmosphere is at least 0.5% and lower than 1.0%.

Figure 3C:
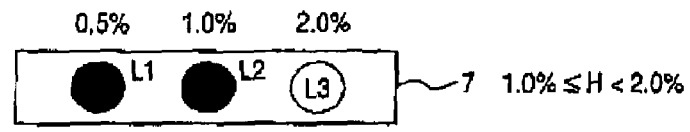
Figure 3D:
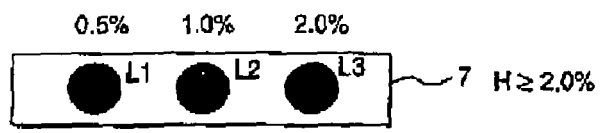

When the hydrogen partial pressure of the atmosphere is at least 0.01 atmosphere and lower than 0.02 atmosphere (B in FIG. 4), the hydrogen partial pressure is higher than or equal to the hydrogen-absorbing pressures of the hydrogen-absorbing alloys MH-1, MH-2. Accordingly, the hydrogen-absorbing alloys MH-1, MH-2 absorb hydrogen and expand in volume; and the respective strain gauges 6 of the detection elements 4A, 4B detect distortion. However, the hydrogen partial pressure is lower than the hydrogen-absorbing pressure of the hydrogen-absorbing alloy MH-3. Accordingly, the hydrogen-absorbing alloy MH-3 does not absorb hydrogen, and the strain gauge 6 of the detection element 4C does not detect distortion. Consequently, as shown in FIG. 3C, the concentration lamps L1, L2 of the display device 7 illuminate, and the concentration lamp L3 does not illuminate. In this case, a hydrogen concentration of the atmosphere is at least 1.0% and lower than 2.0%.

When the hydrogen partial pressure of the atmosphere is 0.02 atmosphere or higher (C in FIG. 4), the hydrogen partial pressure is higher than all the hydrogen-absorbing pressures of the hydrogen-absorbing alloys MH-1, MH-2, MH-3. Accordingly, all of the hydrogen-absorbing alloys MH-1, MH-2, MH-3 absorb hydrogen and expand in volume, and the respective strain gauges 6 of the detection elements 4A, 4B, 4C detect distortion. As a result, all the concentration lamps L1, L2, L3 of the display device 7 illuminate. In this case, a hydrogen concentration of the atmosphere is 2.0% or higher.

Meanwhile, when the hydrogen partial pressure of the atmosphere is lower than the hydrogen discharge pressure of the hydrogen-absorbing alloy, the hydrogen-absorbing alloy storing hydrogen discharges the absorbed hydrogen and reabsorbs its volume before storing hydrogen. Therefore, when the hydrogen partial pressure of the atmosphere is lower than the hydrogen discharge pressure of the hydrogen-absorbing alloy of the detection element 4, the strain gauge 6 of the detection element 4 no longer detects distortion, whereby the concentration lamp L corresponding to the detection element 4 of the display device 7 is illuminated.

In the hydrogen detector 1 of the embodiment, the temperatures of the three detection elements 4A, 4B, 4C, which are formed from the hydrogen-absorbing alloys MH-1, MH-2, MH-3 differ in terms of P-T characteristics, are controlled to substantially the same temperature. Accordingly, a hydrogen concentration can be detected in four levels of concentration ranges. Additionally, temporal changes in hydrogen concentration can also be detected.

The hydrogen detector 1, whose detection elements 4 are formed from hydrogen-absorbing alloys, provides fairly high selectivity for hydrogen, thereby enabling detection of hydrogen concentration with high accuracy. This is considerably advantageous as compared with the case of a catalytic-combustion-type hydrogen sensor which detects hydrogen on the basis of changes in resistance caused when hydrogen to be detected is subjected to catalytic combustion. The catalytic-combustion-type hydrogen sensor may induce catalytic reaction of combustible gases other than hydrogen, which is disadvantageous in terms of selectivity for hydrogen.

In the hydrogen sensors 1 of the embodiments, the operation is conducted at a single temperature. Accordingly, a target value for temperature control is limited to one, whereby the control is fairly easy.

The invention is not limited to the embodiment described hitherto.

For instance, the hitherto-described embodiment takes, as a volume, a physical property which changes during the course of the hydrogen-absorbing alloy storing hydrogen, as well as employing the strain gauge as means for detecting a change in volume; however, the means for detecting the change in volume is not limited to the strain gauge, and may be configured with other appropriate means.

Furthermore, a property which changes upon absorbing of hydrogen by the hydrogen-absorbing alloy may be temperature or weight. In this case, detection means for detecting changes in the property may be configured with temperature detection means or weight detection means.

Furthermore, the number of the detection elements formed from the hydrogen-absorbing alloy is not limited to three, and may be an arbitrary number so long as it is two or more. The greater the number of the detection elements, the greater the number of detectable concentration ranges.

In the hitherto described embodiment, the detection elements are constantly controlled at 100° C.; however, the control temperature is not limited to 100° C., and can be set at an arbitrary temperature.

It will be apparent to those skilled in the art that various modifications and variations can be made to the described preferred embodiments of the present invention without departing from the spirit or scope of the invention. Thus, it is intended that the present invention cover all modifications and variations of this invention consistent with the scope of the appended claims and their equivalents.

What is claimed is:

1. A hydrogen sensor comprising:
   a plurality of detection elements each formed by a differing hydrogen-absorbing alloy, and the alloys further differ from each other in terms of hydrogen-absorbing pressure at a given temperature;
   detection means for detecting changes in a property upon absorbing of hydrogen by the respective detection elements;
   temperature control means for controlling temperatures of all the detection elements to approximately the same value; and
   wherein thermal insulating means is disposed between adjacent detection elements.

2. The hydrogen detector according to claim 1, wherein the property is volume, electrical resistance, or weight.

3. A hydrogen sensor comprising:
   a plurality of detection elements formed by hydrogen-absorbing alloys which differ from each other in terms of hydrogen-absorbing pressure at a given temperature;
   detection means for detecting changes in a property upon absorbing of hydrogen by the respective detection elements;
   temperature control means for controlling temperatures of all the detection elements to approximately the same value; and wherein thermal insulating means is disposed between adjacent detection elements.

4. The hydrogen detector according to claim 3, wherein the property is volume, electrical resistance, or weight.

5. A hydrogen sensor comprising:
a plurality of detection elements formed by hydrogen-absorbing alloys which differ from each other in terms of hydrogen-absorbing pressure at a given temperature;
detectors to detect changes in a property of the alloys upon absorbing of hydrogen by the respective detection elements;
a temperature controller that controls temperatures of all the detection elements to approximately the same value; and
thermal insulators disposed between adjacent detection elements.

6. The hydrogen detector according to claim 5, wherein the property is volume, electrical resistance, or weight.

* * * * *